US007000760B2

(12) United States Patent
Lau

(10) Patent No.: US 7,000,760 B2
(45) Date of Patent: Feb. 21, 2006

(54) JEWELRY BOX WITH A VIEWER

(76) Inventor: Anson W. Lau, 352 Alahmar Ter., San Gabriel, CA (US) 91775

( * ) Notice: Subject to any disclaimer, the term of this patent is extended or adjusted under 35 U.S.C. 154(b) by 181 days.

(21) Appl. No.: 10/407,087

(22) Filed: Apr. 3, 2003

(65) Prior Publication Data

US 2004/0195114 A1    Oct. 7, 2004

(51) Int. Cl.
A45C 11/04    (2006.01)
(52) U.S. Cl. .......................... 206/6.1; 356/30
(58) Field of Classification Search .............. 206/6.1, 206/566, 765, 769, 770, 774, 775–778; 365/30; 359/804
See application file for complete search history.

(56) References Cited

U.S. PATENT DOCUMENTS

| | | | |
|---|---|---|---|
| D24,032 S | 2/1895 | Toman | |
| D27,354 S | 7/1897 | Hill et al. | |
| D113,777 S | 3/1939 | Worssam | |
| 2,248,497 A | 7/1941 | Gelvin | |
| D138,066 S | 6/1944 | Ludel et al. | |
| D199,020 S | 9/1964 | Beddor | |
| 3,410,634 A * | 11/1968 | Buckner | 359/804 |
| 3,740,142 A * | 6/1973 | Takubo | 356/30 |
| 3,982,628 A | 9/1976 | Garcia Rodenas | |
| D267,210 S | 12/1982 | Schwuchow | |
| 4,401,434 A * | 8/1983 | Harris | 206/570 |
| D275,867 S | 10/1984 | Lazzara et al. | |
| D280,147 S | 8/1985 | Wolff | |
| 4,552,264 A * | 11/1985 | Quarrell et al. | 206/6.1 |
| D314,017 S | 1/1991 | Garfinkle | |
| D318,223 S | 7/1991 | Allen | |
| 5,035,324 A | 7/1991 | Bertrand | |
| D319,911 S | 9/1991 | Tsuji | |
| 5,196,966 A * | 3/1993 | Yamashita | 356/30 |
| 5,239,354 A * | 8/1993 | Russell | 356/30 |
| D339,688 S | 9/1993 | Steidl | |
| 5,260,763 A * | 11/1993 | Yamashita | 356/30 |
| D350,427 S | 9/1994 | Vig et al. | |
| 5,358,099 A * | 10/1994 | Tavone | 206/6.1 |
| D373,078 S | 8/1996 | Cheng | |
| D386,305 S | 11/1997 | Lau | |
| D386,400 S | 11/1997 | Lau | |
| D422,643 S | 4/2000 | Goslin et al. | |
| D425,566 S | 5/2000 | Mueller et al. | |
| D447,518 S | 9/2001 | Lau | |
| 6,378,696 B1 * | 4/2002 | Smouha | 206/6.1 |

* cited by examiner

Primary Examiner—Luan K. Bui
(74) Attorney, Agent, or Firm—Sheldon & Mak; Marc Karish

(57) ABSTRACT

A container has a base including a support for an object to be viewed. A container also has a lid on top of the base, the lid having a light-conveying portion for illuminating an object to be viewed and a magnifying viewer for viewing an object to be viewed.

19 Claims, 3 Drawing Sheets

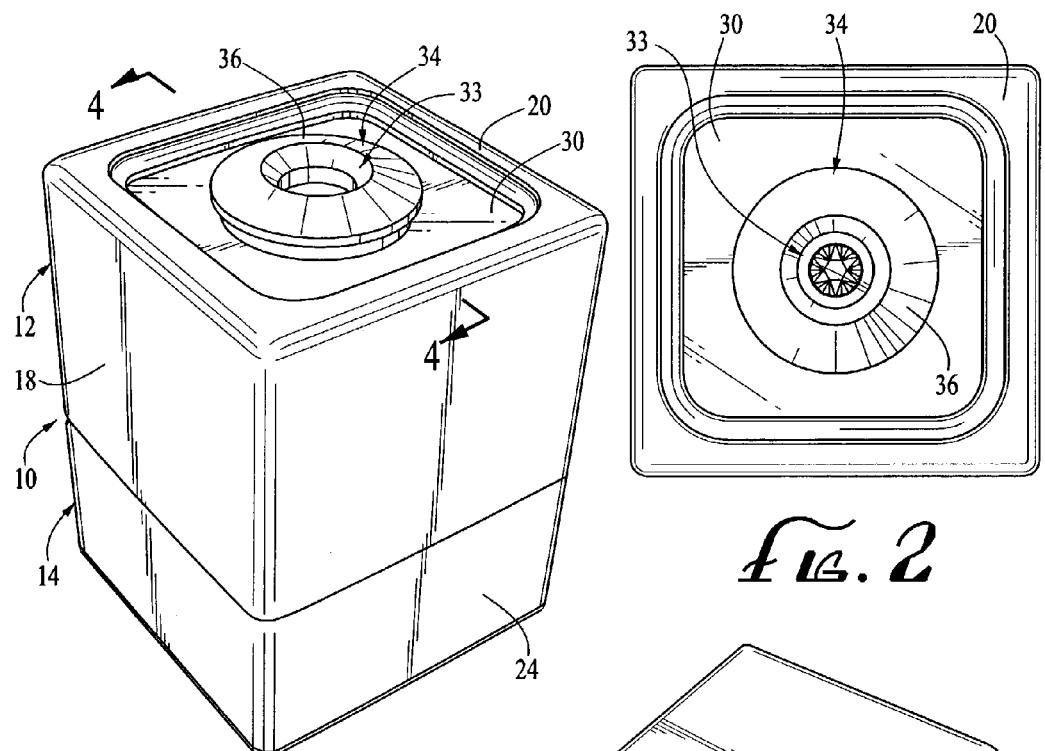
FIG. 1
FIG. 2
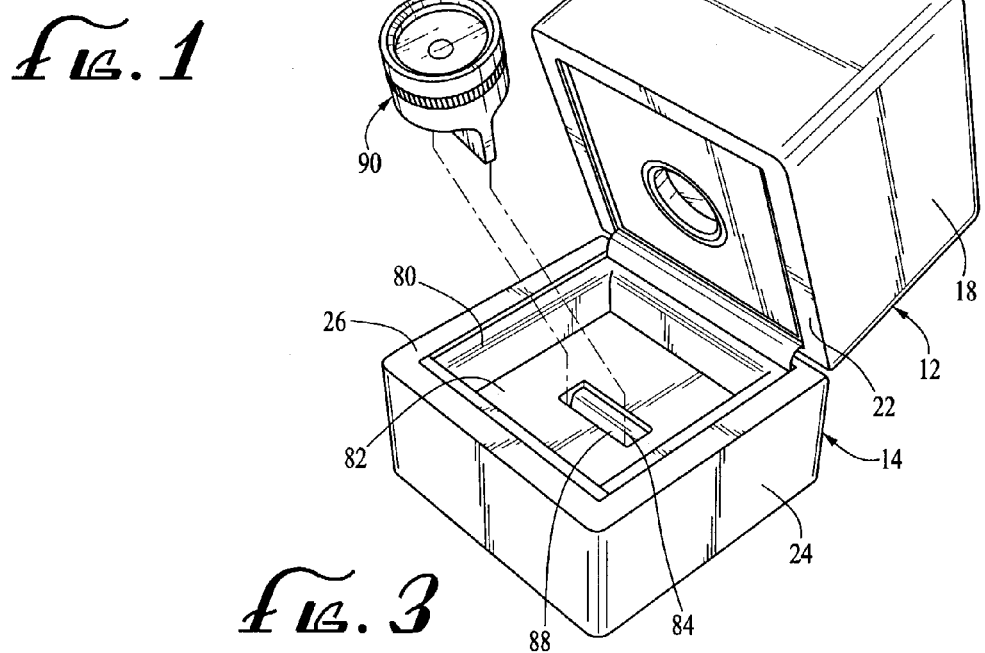
FIG. 3

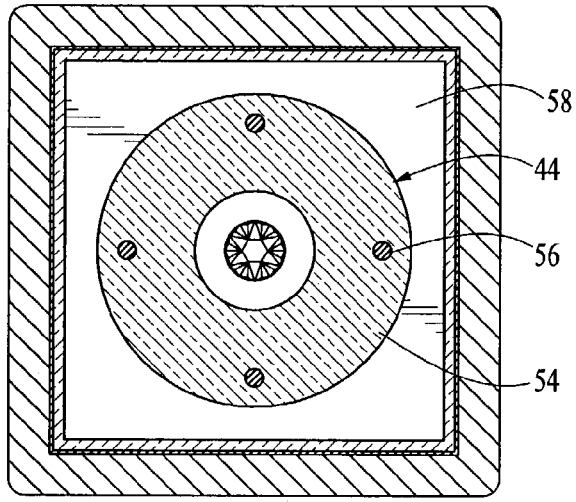
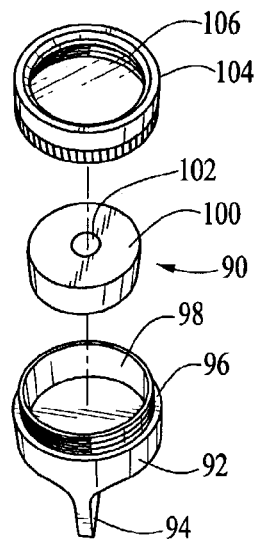
fig.8
fig.6
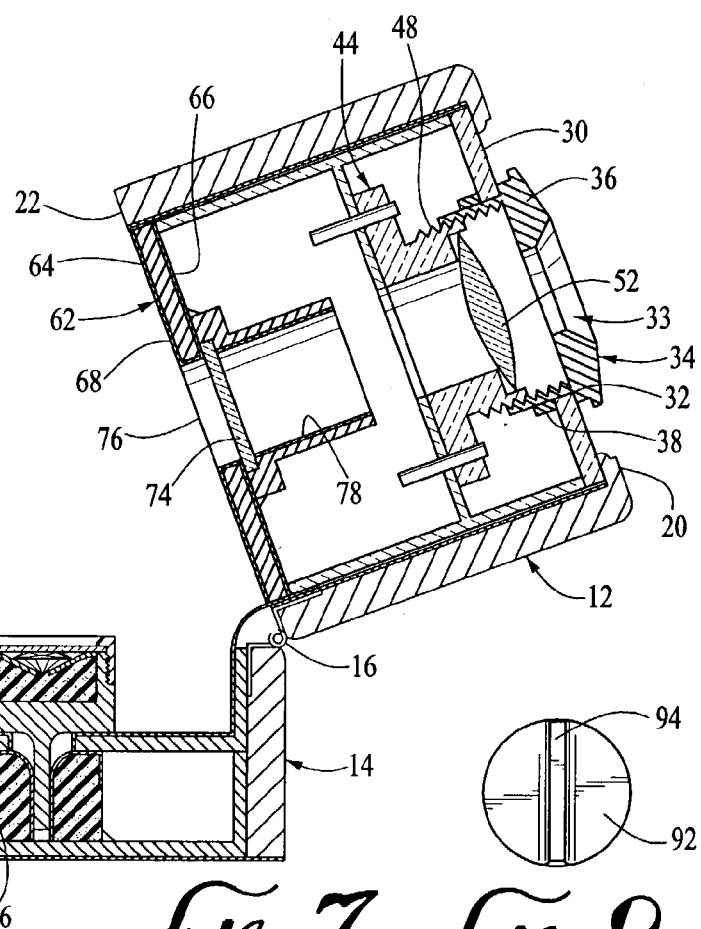
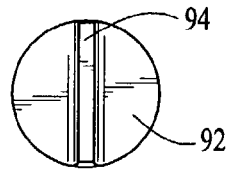
fig.7  fig.9

JEWELRY BOX WITH A VIEWER

RELATED APPLICATION

This application is being filed on the same date as a design patent application of the same inventor, entitled JEWELRY BOX WITH A VIEWER, which is hereby incorporated herein by reference.

BACKGROUND

The present invention relates to a container and more particularly to a container having a magnifying viewer and a light-conveying portion so that the contents of the container may be viewed when the container is in a closed condition.

Traditionally, a diamond ring is stored and displayed in a jewelry box. The ring is inserted into a mount that is contained in a chamber of the jewelry box. Increasingly, gemstones and rings are being manufactured with very small details which, when viewed, function to help sell the ring or gemstone. However, in order to view the very small details a viewing device outside of a jewelr-y box must be employed. Once placed in a closed jewelry box, the ring or gemstone is unviewable. The removal of the gemstone or ring from the box for viewing increases the likelihood of loss or theft. Therefore, there exists a need for viewing the details of gemstones or rings without additional viewing devices and without removal of the gemstone or ring from a jewelry box.

SUMMARY

Accordingly, the present invention is directed to a container having a base with a support for an object to be viewed. The container also has lid with a light conveying portion for illuminating such an object and a magnifying viewer for viewing the object. Optionally, a hinge is coupled to the lid and to the base. In a preferred embodiment, the lid also includes a shelf having a plurality of orifices. The magnifying viewer further includes an eyepiece rotatably coupled to the lid. The eyepiece has a threaded portion and defines a cylinder through which light may pass.

A platform is coupled to the eyepiece. The platform has a threaded portion that engages with the threaded portion of the eyepiece. The platform also has a plurality of posts, each post being moveably engageable in one of the orifices in the shelf. A magnifying lens is coupled to the platform. Rotation of the eyepiece moves the platform and the magnifying lens to change focus. In a version, the light-conveying portion is located in the top of the lid and the eyepiece is mounted in the light-conveying portion. In an alternate version, the light-conveying portion is located in the top and/or at least one side of the lid.

Additionally, the lid has a bottom panel. The bottom panel has a top surface, a bottom surface and an orifice. A tube is mounted to the top surface of the bottom panel. The tube has a recessed portion and a lens mounted in the recessed portion. The magnifying viewer, tube and orifice are aligned to allow light to pass through the tube into the base and to allow an object in the base to be seen through the magnifying viewer. Optionally, the tube has a liner to restrict the color of light transmitted to the base.

Optionally, the support in the base is a slot positioned below the orifice of the bottom panel. The slot is dimensioned to allow placement of an object in the slot to position a portion of the object to be seen through the magnifying viewer.

The present invention is also directed to a caddy that is removeably mountable in the slot. In a preferred embodiment, the caddy has a body, the body having a tab engageable in the slot of the base, a threaded portion, and a recessed portion. The caddy also has an insert mountable in the recessed portion of the body. The caddy also has a cap having a transparent portion and threads engageable with the threaded portion of the body.

BRIEF DESCRIPTION OF THE DRAWINGS

A better understanding of the present invention will be had with reference to the accompanying drawings in which:

FIG. 1 is a top front perspective view of a jewelry box in a closed condition according to a preferred embodiment of the present invention;

FIG. 2 is a top plan view of the jewelry box of FIG. 1;

FIG. 3 is a top front perspective view of the jewelry box of FIG. 1 in an open condition showing a caddy according to an embodiment of the present invention;

FIG. 6 is a cross sectional view of a jewelry box taken along line 6—6 of FIG. 4;

FIG. 7 is a cross sectional view of the jewelry box of FIG. 4 in a partially open condition;

FIG. 8 is a top front exploded view of the caddy shown in FIG. 3; and

FIG. 9 is a bottom plan view of the caddy shown in FIG. 3.

DETAILED DESCRIPTION

Figure 4:
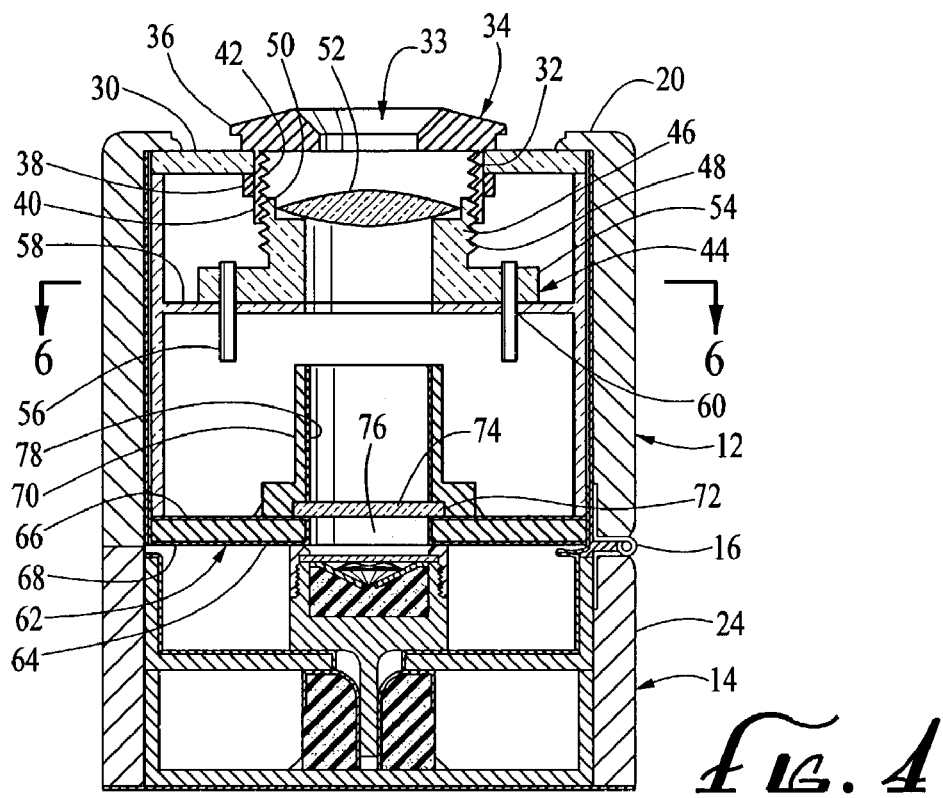
FIG. 4 is a cross sectional view of the jewelry box of FIG. 1 taken along line 4—4 of FIG. 1 showing the lens in a lowered position.

With reference to FIGS. 1 to 7 of the drawings, a container 10 according to a preferred embodiment of the present invention is illustrated. The container 10 is adapted for storing and displaying rings, gemstones and other small objects such as coins and stamps. Although able to store numerous types of objects, because the container 10 is suitable as a jewelry box, the container will be referred to herein as a jewelry box. For illustrative purposes a gemstone is shown in FIGS. 2 and 4 to 7. The jewelry box comprises a lid 12 and a base 14 connected to each other via a hinge 16. Optionally, the lid 12 and the base 14 may be connected through other connecting means, such as threads or clasps.

The lid has four walls 18, a top 20, and a bottom 22. The base has four walls 24, a top 26, and a bottom 28. The box has a closed condition, as shown in FIG. 1 in which the bottom 22 of the lid 12 engages the top 26 of the base 14. The box has an open condition, as shown in FIG. 3, wherein the bottom 22 of the lid 12 is disengaged from the top 26 of the base 14.

Considering the lid in more detail, as shown in FIGS. 1 to 7, the top of the lid has a light-conveying portion 30 and an orifice 32. The light-conveying portion 30 allows light to enter the box 10, when the box 10 is in the closed condition. In additional versions, the light-conveying portion is located on one or more sides 18 of the lid. Optionally, the light-conveying portion is made of a semi-transparent plastic or glass. Optionally, the light-conveying portion includes a user activated light, such as a light emitting diode.

Figure 5:
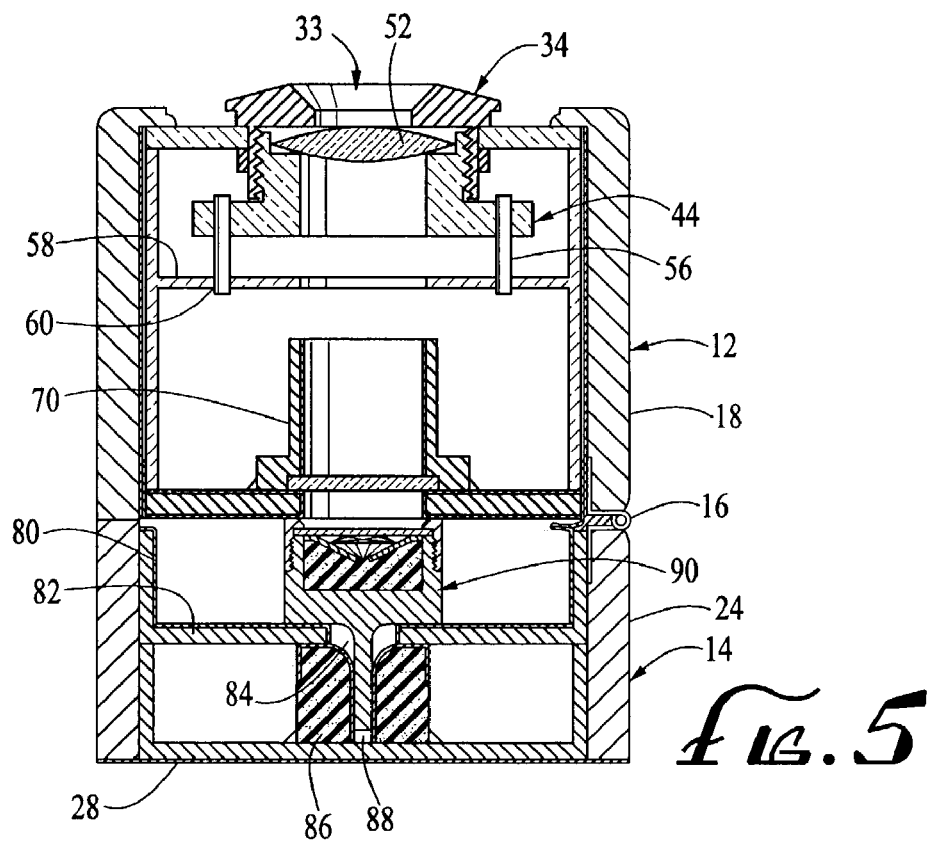
FIG. 5 is a cross sectional view of the jewelry box of FIG. 1 taken along line 4—4 of FIG. 1 showing the lens in a raised position.

A magnifying viewer 33 is mounted in the lid. In a preferred embodiment, the magnifying viewer has an eyepiece 34 rotatably mounted in the orifice 32 on the top of the lid. As shown in FIGS. 4 and 5, the eyepiece 34 has an outer portion 36 that sits on the outside of the top of the lid and an inner portion 38 that sits on the inside of the top of the lid. Both the outer portion 36 and the inner portion 38 have a diameter larger than the orifice 32 in the top of the lid to prevent the eyepiece from being removed from the orifice. The eyepiece has a threaded portion 40 coupled to the outer portion 36 and the inner portion 38. The threaded portion 40 has internal threads 42. The eyepiece 34 defines a cylinder through which light may pass.

In a preferred embodiment, the magnifying viewer 33 also has a platform 44. The platform 44 has a threaded portion 46 and is moveably mounted to the threaded portion 40 of the eyepiece 34. The threaded portion 46 of the platform 44 has external threads 48 that mate with the internal threads 42 of the threaded portion 40 of the eyepiece. The platform 44 has a recessed portion 50. A magnifying lens 52 is mounted in the recessed portion 50. In a preferred embodiment, the magnifying lens 52 is a convex lens having an object space focal length greater than or equal to the distance from the lens to the object to be viewed. The platform 44 also has a flange 54. The flange 54 has a plurality of posts 56.

A shelf 58 extends across the lid 12. In a preferred embodiment, the shelf 58 is made of a transparent material. The shelf 58 has a plurality of holes 60. The posts 56 of the platform 44 are moveably mounted within the holes 60 of the shelf 58. The mounting of the posts 56 in the holes 60 prevents the rotation of the platform 44. Rotation of the eyepiece 34 causes the platform 44 and the lens 52 to be moved toward or away from the top of the lid 12 to change focus. The adjustable focus allows for enhanced viewing of special gemstone cuts, such as heart or arrow cut diamonds.

As shown in FIG. 4, a lowermost position of the platform is defined when the flange 54 of the platform 44 engages the shelf 58. As shown in FIG. 5, an uppermost position of the platform 44 is defined when the flange 54 of the platform 44 engages the threaded portion 40 of the eyepiece 34. Optionally, the magnifying viewer 33 may be fixed rather than rotatably adjustable to change the focus. In an alternative embodiment, the magnifying viewer 33 has the magnifying lens 52 coupled to the eyepiece 34 without a platform. In another embodiment, the top of the lid includes an injection molded plastic magnifying lens as the magnifying viewer 33.

In a preferred embodiment, the bottom of the lid 12 has a panel 62. The panel 62 has a lower surface 64 and an upper surface 66. The lower surface 64 faces the base 14. Optionally, the lower surface 64 may be covered in felt 68. A flanged tube 70 is mounted to the upper surface 66. The flanged tube 70 has a recess 72. Optionally, a lens 74 is mounted in the recess 72. The lens 74 may be a plain sheet of plastic or glass to close the lid from contaminants. Alternatively, the lens 74 may be designed to provide a compound magnification effect with the magnifying lens 52 on the platform 44.

The panel 62 also has a hole 76 corresponding to the diameter of the tube 70. The tube 70 allows light to pass through the hole 76 to the base 14. Optionally, the tube 70 may be lined with a colored insert 78 to reflect light of a desired wavelength and color to the base 14. Different colored inserts may be employed for enhanced viewing of special gemstone cuts, such as heart or arrow cut diamonds. In a version, the tube 70 contains a blue colored metal insert.

The base 14 defines an interior cavity. Optionally, the interior cavity is lined with a liner 80, such as felt. The felt may be a specific color to enhance viewing of the contents of the box. A shelf 82 extends across the base 14. The shelf has an orifice 84. A stage 86 is mounted between the bottom of the base 14 and the shelf 82. The stage 86 supports an object to be viewed. Optionally, the stage 86 is made from a mechanically deformable material such as foam and lined with a liner such as felt. The stage 86 has a slot 88. The slot 88 is sized so that a ring may be placed into the slot such that a gemstone attached to the ring is oriented facing upwards toward the lid. Alternatively, a gemstone may be placed into a caddy 90 which is then placed into the slot 88.

A caddy 90 according to a preferred embodiment of the present invention is illustrated in FIGS. 3 to 5 and 7 to 9. The caddy 90 has a body 92. The body 92 has a tab 94 engageable in the slot 88 of the stage 86. The tab 94 may be formed in a variety of shapes and sizes depending on the size and shape of the slot. The body 92 also has a threaded portion 96 and a recessed portion 98. An insert 100 is mounted in the recessed portion 96. Optionally, the insert 100 is made from a mechanically deformable material, such as foam, and may be covered with felt. Additionally, the insert 100 may have a recessed portion 102 for placement of an object such as a gemstone.

A cap 104 is removeably mounted to the body 92. The cap 104 has interior threads 106 that engage with the threaded portion 96 of the body. The cap 104 has a transparent portion allowing the contents of the caddy 90 placed on the insert 100 to be viewed once the cap 104 is screwed onto the body 92. The body 92 and the cap 104 are preferably made from metal, such as aluminum. Alternatively the body 92 and the cap are made of injection molded plastic.

Although the jewelry box described has a rectangular shape, the jewelry box may be made in any size and shape such as circular or oval. The jewelry box can be made of numerous materials, such as wood, metal, and plastic. However, the preferred material is injection molded plastic because of the ease and low cost of construction. The exterior of the jewelry box may be artistically decorated. Additionally, the exterior may be colored and textured to resemble wood or metal. Optionally, the bottom 28 of the base 14 is covered with rubber to prevent the box 10 from slipping across a surface.

Although the present invention has been described with considerable detail with reference to certain preferred versions thereof, other versions are possible. Therefore, the spirit and scope of the appended claims should not be limited to the description of the preferred version as described herein. All features disclosed in the specification, including the claims, abstract, and drawings maybe combined in any combination except combinations where at least some of the features are mutually exclusive. Each feature disclosed in the specification, including the claims, abstract, and drawings, can be replaced by alternative features serving the same, equivalent or similar purpose, unless expressly stated otherwise. Thus unless expressly stated otherwise, each feature disclosed is one example only of a generic series of equivalent or similar features.

Any element in a claim that does not explicitly state "means" for performing a specified function or "step" for performing a specified function should not be interpreted as a "means" or "step" clause as specified in 35 U.S.C. §112.

What is claimed is:

1. A container comprising:
 a base including a support for an object to be viewed; and
 a lid on top of the base, the lid comprising:
  a light-conveying portion for illuminating such an object;
  a shelf, the shelf having a plurality of orifices; and
  a magnifying viewer for viewing the object, the magnifying viewer further comprising:
   an eyepiece rotatably coupled to the lid, the eyepiece having a threaded portion and defining a cylinder through which light may pass;

a platform coupled to the eyepiece, the platform having a threaded portion engageable with the threaded portion of the eyepiece and a plurality of posts, each post being moveably engageable in a one of the plurality of orifices in the shelf; and a magnifying lens coupled to the platform; and wherein rotation of the eyepiece moves the platform and the magnifying lens to change focus.

2. The container of claim 1 wherein the lid has a top, the top comprising the light-conveying portion; and wherein the eyepiece is mounted in the light-conveying portion.

3. The container of claim 1 wherein the lid has a top and a plurality of sides;

and wherein at least one of the top and the plurality of sides comprise the light-conveying portion.

4. The container of claim 1 wherein the lid further comprises:

a bottom panel, the bottom panel having a top surface, a bottom surface and an orifice;

a tube mounted to the top surface of the bottom panel, the tube having a recessed portion; and a lens mounted in the recessed portion of the tube;

wherein the magnifying viewer, tube and orifice are aligned to allow light to pass through the tube into the base and to allow an object in the base to be seen through the magnifying viewer.

5. The container of claim 4 wherein the tube has a liner to restrict the color of light transmitted to the base.

6. The container of claim 5 wherein the support comprises a slot positioned below the orifice of the bottom panel; the slot being dimensioned to allow placement of an object to be viewed in the slot to position a portion of the object to be seen through the magnifying viewer.

7. The container of claim 6 further comprising a caddy removeably mountable in the slot.

8. The container of claim 7 wherein the caddy further comprises:

a body, the body having a tab engageable in the slot of the base, a threaded portion, and a recessed portion;

an insert mountable in the recessed portion of the body; and a cap having a transparent portion and threads engageable with the threaded portion of the body.

9. The container of claim 4 wherein the base further comprises:

a bottom; and a shelf, the shelf having an orifice; and wherein the support further comprises a stage mounted between the shelf and the bottom below the orifice of the shelf, the stage comprising a slot dimensioned to allow placement of an object to be viewed in the slot to position a portion of the object to be seen through the magnifying viewer.

10. The container of claim 9 further comprising a caddy removeably mountable in the slot.

11. The container of claim 10 wherein the caddy further comprises:

a body, the body having a tab engageable in the slot, a threaded portion, and a recessed portion;

an insert mountable in the recessed portion of the body; and a cap having a transparent portion and threads engageable with the threaded portion of the body.

12. The container of claim 1 wherein the container has an open condition and a closed condition and contents of the container are viewable through the magnifying lens when the container is in the closed condition.

13. A container comprising:

a lid, the lid having a top, a bottom, a plurality of sides, and a shelf positioned between the top and the bottom;

a base connectable to the lid, the base having a top, a bottom, a shelf positioned between the top and the bottom; and a stage positioned between the shelf and the bottom;

a magnifying viewer positioned in the lid top; and wherein at least one of the lid top and the plurality of lid sides comprise a light-conveying portion; and wherein the stage comprises a slot.

14. The container of claim 13 further comprising a hinge coupled to the lid and the base.

15. The container of claim 13 wherein the lid shelf comprises a plurality of orifices and wherein the magnifying viewer further comprises:

an eyepiece rotatably mounted to the lid top, the eyepiece having a threaded portion;

a platform having a threaded portion engaging with the threaded portion of the eyepiece and a plurality of posts each post being moveably engageable in a one of the plurality of orifices in the shelf; and a magnifying lens coupled to the platform;

wherein rotation of the eyepiece moves the platform and lens to change focus.

16. The container of claim 15 wherein the lid further comprises:

a bottom panel, the bottom panel having a top surface, a bottom surface and an orifice;

a tube mounted to the top surface of the bottom panel, the tube having a colored liner and a recessed portion; and a lens mounted in the recessed portion of the tube;

wherein the magnifying viewer, tube and orifice are aligned to allow light to pass through the tube into the base and to allow an object in the base to be seen through the magnifying viewer.

17. The container of claim 13 further comprising a caddy removeably mountable in the slot of the stage.

18. A container comprising:

a lid, the lid having a top, a bottom, a plurality of sides, a light-conveying portion, and a shelf positioned between the top and the bottom, the shelf having a plurality of orifices;

a magnifying viewer positioned in the lid top, the magnifying viewer comprising an eyepiece rotatably mounted to the lid top, the eyepiece having a threaded portion;

a platform having a threaded portion engaging with the threaded portion of the eyepiece and a plurality of posts, each post being moveably engageable in a one of the plurality of orifices in the shelf; and a magnifying lens coupled to the platform;

a tube mounted to the bottom of the lid, the tube having a colored liner;

a hinge coupled to the lid;

a base coupled to the hinge, the base having a top, a bottom, a shelf positioned between the top and the bottom; and a stage positioned between the shelf and the bottom;

wherein the stage comprises a slot.

19. The container of claim 18 further comprising a caddy removeably mountable in the slot of the stage.

* * * * *